US00PP25058P3

(12) United States Plant Patent
de Boer

(10) Patent No.: US PP25,058 P3
(45) Date of Patent: Nov. 11, 2014

(54) ***NEPHROLEPIS* PLANT NAMED 'GREEN DELIGHT'**

(50) Latin Name: *Nephrolepis exaltata*
Varietal Denomination: Green Delight

(75) Inventor: Petrus de Boer, Asten (NL)

(73) Assignee: Gebr. de Boer VOF (NL)

( * ) Notice: Subject to any disclaimer, the term of this patent is extended or adjusted under 35 U.S.C. 154(b) by 151 days.

(21) Appl. No.: 13/507,705

(22) Filed: Jul. 20, 2012

(65) Prior Publication Data

US 2014/0026277 P1 Jan. 23, 2014

(51) Int. Cl.
*A01H 5/00* (2006.01)

(52) U.S. Cl.
USPC ..... Plt./379

(58) Field of Classification Search
USPC ..... Plt./379
See application file for complete search history.

*Primary Examiner* — Kent L Bell
(74) *Attorney, Agent, or Firm* — Cassandra Bright

(57) ABSTRACT

A new and distinct *Nephrolepis exaltata* cultivar named 'Green Delight' is disclosed, characterized by hard, green foliage with reduced frond abscission, slow, upright growth form. The new variety is a *Nephrolepis exaltata*, typically produced as an indoor ornamental plant.

1 Drawing Sheet

Latin name of the genus and species: *Nephrolepis exaltata*.
Variety denomination: 'Green Delight'.

BACKGROUND OF THE INVENTION

The new cultivar is the product of chance discovery. The new variety originated as a naturally occurring whole plant mutation of the unpatented 'Boston Blue Bell' variety of *Nephrolepis exaltata*.

The new variety was discovered by the inventor, Petrus de Boer, a citizen of the Netherlands, during Spring 2006 in a commercial greenhouse belonging to the inventor in Asten, The Netherlands. After identifying the new variety as a potentially interesting selection, the inventor continued confidential testing and propagation of 'Green Delight', assessing the stability of the unique characteristics of this variety.

Asexual reproduction of the new cultivar 'Green Delight' was first performed at a lab in Burgh-haamstede, The Netherlands, by tissue culture in May of 2011. Access to all plants was restricted, as plants were kept in a location that is not open to the public. Through subsequent propagation by tissue culture, multiple generations have been reproduced, which have shown that the unique features of this cultivar are stable and reproduced true to type.

SUMMARY OF THE INVENTION

The cultivar 'Green Delight' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Green Delight'. These characteristics in combination distinguish 'Green Delight' as a new and distinct *Nephrolepis exaltata* cultivar:

1. Green fronds.
2. Strong, hard fronds.
3. Reduced frond abscission.

4. Upright growth form.
5. Slower growth rate.

PARENT COMPARISON

Plants of the new cultivar 'Green Delight' are similar to the parent, *Nephrolepis exaltata* 'Boston Blue Bell' in most horticultural characteristics. The new variety, however, possesses harder fronds that are green in color whereas 'Boston Blue Bell' possesses leaves that are softer and yellow-green. 'Green Delight' is more upright in growth than 'Boston Blue Bell' as well as slower growing. Fronds of 'Green Delight' have much less abscission, are glossier, and rounded at the tips compared to 'Boston Blue Bell'.

COMMERCIAL COMPARISON

Plants of the new cultivar 'Green Delight' are similar to the commercial variety *Nephrolepis exaltata* 'Sassy' in most horticultural characteristics. Plants of the new variety, however, grow more upright, and more slowly than plants of 'Sassy'.

Plants of the new cultivar 'Green Moment' are also comparable to the commercial variety *Nephrolepis exaltata* 'Green Delight', filed concurrently, U.S. application Ser. No. 13/507,705, in most horticultural characteristics. Plants of 'Green Moment', however, grow more slowly and produce darker green foliage, emerging at a less acute angle.

BRIEF DESCRIPTION OF THE PHOTOGRAPH

The accompanying photograph in FIG. 1 illustrates in full color a typical plant of 'Green Delight' grown in a commercial greenhouse in Asten, The Netherlands. This plant is approximately 22 weeks old, shown planted in a 17 cm. container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'Green Delight' plants grown in a greenhouse in Asten, The Netherlands. This was done in June 2012 with a plant 22 weeks old. Temperatures ranged from 18° C. at night to 20° C. during the day. No artificial light, photoperiodic treatments were given to the plants. No chemical treatments were given to plants. Measurements and numerical values represent averages of typical plant types.

Botanical classification: *Nephrolepis exaltata* 'Green Delight'.

PROPAGATION

Time to initiate roots: Approximately 21-28 days from a rooted plantlet at approximately 22° C.

Time to produce rooted plantlet: Approximately 5 weeks at approximately 22° C.

Root description: Very dense and freely branching, moderately fine, slightly fibrous, non-fleshy, colored near Brown: RHS 199D.

PLANT

Growth habit: Broad upright.

Plant shape: Inverted triangle.

Height: Approximately 34.0 cm.

Plant spread: Approximately 53.0 cm.

Growth rate: Moderate to high.

Branching characteristics: No branches, fronds grow directly from the base/rootstock.

Frond arrangement: Irregular.

FOLIAGE

Frond:

*Quantity per plant*.—Average 100.

*Frond type*.—Compound, pinnate. Pinnae per Frond: Average 46. Average Frond Length: Approximately 23.9 cm. Average Frond Width: Approximately 6.4 cm. Average Pinnae Length: Approximately 7.2 cm. Average Pinnae Width: At base approximately 1.4 cm. At mid-section approximately 0.9 cm. Pinnae shape: Lanceolate. Pinnae Apex: Obtuse. Pinnae Base: Truncate. Overall Frond Shape: Lanceolate. Margin: Entire. Aspect: Slightly wavy, tip moderately curved downwards.

*Texture of top surface*.—Smooth, moderately glossy.

*Texture of bottom surface*.—Smooth, slightly glossy.

*Color*.—Young, foliage upper side: Yellow-green; near RHS 144A. Young foliage under side: Yellow-green; near RHS 144A. Mature foliage upper side: Green; in between near RHS 137B and 141A. Mature foliage under side: Green; near RHS 137B.

Venation:

*Type*.—Pinnate.

*Venation coloration upper side*.—Green; near RHS N137A.

*Venation coloration under side*.—Yellow-green; near RHS 146A.

Petiole:

*Length*.—Approximately 7.0 cm.

*Width*.—At geniculum: Approximately 0.12 cm. Above clump: Approximately 0.12 cm.

*Color*.—Proximal part, Brown; near RHS 200A and 200B, middle part Yellow-green; RHS 152B and 152C, distal part Yellow-green; near RHS 144A.

*Strength*.—Strong.

Pinnae petiole: Not present.

Rachis description:

*Length*.—Approximately 23.5 cm.

*Width*.—Approximately 0.1 cm.

*Color*.—Upper side Yellow-green; near RHS 144A, lower side slightly lighter; near RHS 144B.

*Strength*.—Strong.

*Texture*.—Moderately glossy, sparsely covered with tufts of short soft hairs, average length 0.2 cm, coloured Greyed-white; near RHS 156D.

Other foliage characteristics: No.

OTHER CHARACTERISTICS

Spore production: No.

Temperature tolerance: Indoor fern, hardy to at least USDA zone 10.

Drought tolerance: Can go without water for at least a week.

Disease/pest resistance: Typical of *Nephrolepis exaltata*.

What is claimed is:

1. A new and distinct cultivar of *Nephrolepis exaltata* plant named 'Green Delight' as herein illustrated and described.

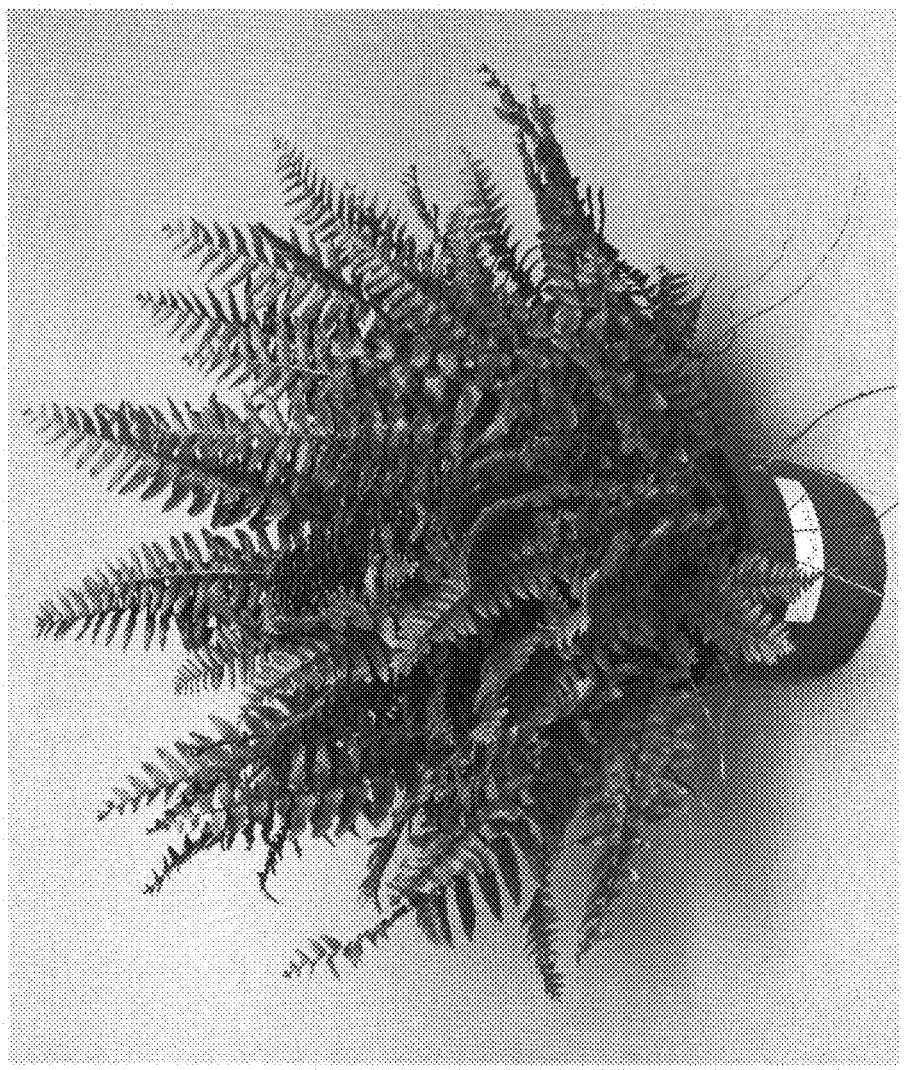

* * * * *